United States Patent [19]

Mantegani et al.

[11] Patent Number: 5,430,031
[45] Date of Patent: Jul. 4, 1995

[54] SEROTONINERGIC ERGOLINE DERIVATIVES

[75] Inventors: Sergio Mantegani, Milan; Enzo Brambilla, Mariano Comense; Carla Caccia, Gallarate; Nicola Carfagna, Nerviano, all of Italy

[73] Assignee: Farmitalia Carlo Erba S.r.l., Milan, Italy

[21] Appl. No.: 169,177

[22] Filed: Dec. 20, 1993

[30] Foreign Application Priority Data

Dec. 24, 1992 [GB] United Kingdom ................. 9226967
Mar. 19, 1993 [GB] United Kingdom ................. 9305696

[51] Int. Cl.6 ................. A61K 31/48; A61K 31/495; A61K 31/505; C07D 403/14
[52] U.S. Cl. .................... 514/253; 514/252; 514/288; 544/238; 544/310; 544/333; 544/405; 546/67; 546/68; 546/69
[58] Field of Search .............. 546/67, 68, 69; 544/238, 310, 333, 405; 514/288, 253, 252

[56] References Cited

U.S. PATENT DOCUMENTS

| | | | |
|---|---|---|---|
| 4,248,871 | 2/1981 | Stadler | 546/69 |
| 4,382,940 | 5/1983 | Bernardi et al. | 514/288 |
| 4,675,404 | 6/1987 | Bernardi et al. | 514/288 |
| 4,681,880 | 7/1987 | Kobel et al. | 546/69 |
| 4,690,929 | 9/1987 | Bernardi et al. | 546/69 |
| 4,728,649 | 3/1988 | Mantegani et al. | 514/288 |
| 4,746,666 | 5/1988 | Bernardi et al. | 514/288 |
| 4,785,001 | 11/1988 | Temperilli et al. | 514/288 |
| 4,839,363 | 6/1989 | Brambilla et al. | 514/288 |
| 4,843,703 | 7/1989 | Nolte et al. | 514/288 |
| 4,847,253 | 7/1989 | Buonamici et al. | 514/288 |
| 4,857,298 | 8/1989 | Wachtel et al. | 546/68 |
| 4,859,678 | 8/1989 | Mantegani et al. | 546/67 |
| 4,863,929 | 9/1989 | Sauer et al. | 546/68 |
| 4,874,768 | 10/1989 | Huth et al. | 546/67 |
| 4,902,691 | 2/1990 | Cohen et al. | 546/69 |
| 4,931,447 | 6/1990 | Foreman et al. | 546/69 |
| 4,939,258 | 7/1990 | Whitlen et al. | 546/67 |
| 4,968,801 | 11/1990 | Sauer et al. | 546/69 |
| 4,968,802 | 11/1990 | Garbrecht et al. | 546/69 |
| 5,202,325 | 4/1993 | Rossi et al. | 514/288 |
| 5,210,194 | 5/1993 | Mantegani et al. | 514/288 |
| 5,219,862 | 6/1993 | Sauer et al. | 546/69 |

FOREIGN PATENT DOCUMENTS

| | | | |
|---|---|---|---|
| 0070562 | 1/1983 | European Pat. Off. | |
| 0082805 | 6/1983 | European Pat. Off. | |
| 118848 | 9/1984 | European Pat. Off. | 546/68 |
| 0197241 | 10/1986 | European Pat. Off. | |
| 351351 | 1/1990 | European Pat. Off. | 546/68 |
| 3620293 | 12/1987 | Germany | 546/68 |

OTHER PUBLICATIONS

Ergot Alklakoids and Related Compounds Edited by Berde et al (1978). pp. 37–61, 533 and 560.

*Primary Examiner*—Cecilia Tsang
*Attorney, Agent, or Firm*—Oblon, Spivak, McClelland, Maier & Neustadt

[57] ABSTRACT

The present invention provides compounds of the formula (I)

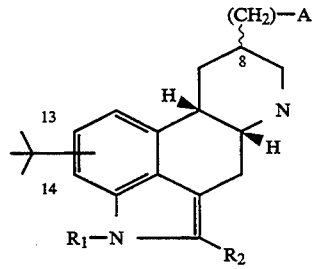

wherein A, $R_1$, $R_2$ and $R_3$ are defined as in the specification, or a pharmaceutically acceptable salt thereof. A process for their preparation and the pharmacetical compositions comprising them are also provided.

8 Claims, No Drawings

SEROTONINERGIC ERGOLINE DERIVATIVES

The present invention relates to novel tert-butylergoline derivatives, to a process for their production, to a pharmaceutical composition containing them and to their use as pharmaceuticals.

The present invention provides a novel group of ergoline derivatives, which have been found to possess special interesting biological activity.

The disclosed compounds have selective and high affinity for 5-HT$_{1A}$ receptors and differ notably from most other ergoline derivatives in that they display a negligible affinity for $\alpha_1$, $\alpha_2$, D$_1$, D$_2$ receptors.

The said compounds can be used for the treatment of various disorders associated with serotoninergic disfunctions, such as impairment of thermoregulation, memory function, sleep disorders, satiety control (i.e. consumption of food and of beverages.), drugs addiction, control of drug withdrawal, hypertension, hyperemesis, depression, anxiety and psychosis, ischemic insult.

More particularly the present invention provides a compound of formula (I)

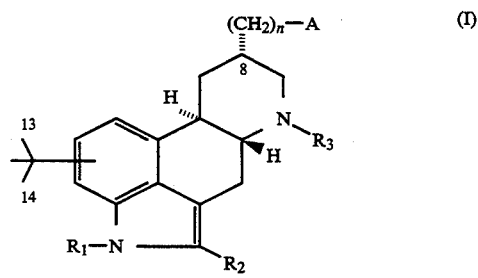

wherein A represents OH, NH$_2$, COOR$_3'$, OCONHR$_4$, CONHR$_4$, NHCOR$_4$, NHCO$_2$R$_4$, NHC(X)NHR$_4$, NHC(X)NHCOR$_4$,

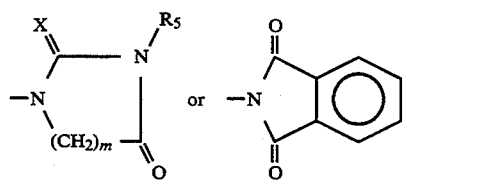

R$_1$ is hydrogen or C$_{1-4}$ linear or branched alkyl; R$_2$ is hydrogen, chlorine, bromine or an S-C$_{1-4}$ alkyl group; R$_3$ and R$_3'$ are, independently, C$_{1-5}$ alkyl or hydrogen, n is 0,1 or 2; m is 1 or 2; R$_4$ is hydrogen, C$_{1-7}$ alkyl, C$_{3-7}$ cycloalkyl, adamantidyl (tricyclo 3.3.1.1.$^{3,7}$) decan-1-yl), C$_{1-5}$ alkylphenyl, C$_2$ alkenylphenyl, C$_2$ alkynylphenyl, phenyl optionally substituted by one or more groups selected from C$_{1-4}$ alkyl, C$_{1-3}$ alkoxy, methylendioxy, cyano, trifluoromethyl, hydroxy, nitro and acetyl; an optionally substituted naphthyl ring or phenyl condensed with a heterocyclic ring system having 5- or 6- ring members including 1 to 4 heteroatoms selected from nitrogen, oxygen and sulphur; a heterocyclic ring having 5 or 6 ring members including 1 or 2 heteroatoms selected from nitrogen, oxygen and sulphur which is optionally substituted by a group selected from C$_{1-4}$ alkyl, phenyl optionally substituted as defined above, C$_{1-3}$ alkoxy and halogen; R$_5$ is hydrogen, C$_{1-4}$ alkyl or phenyl and X is NH, O or S; or a pharmaceutically acceptable salt thereof.

A halogen is preferably chlorine or bromine. The t-butyl substituent is at position 13 or 14 of the ergoline framework. The substituent at position 8 is α or β.

Suitable pharmaceutically acceptable acid addition salts include salts with both inorganic and organic acids.

In the present specification, the term linear or branched alkyl includes methyl, ethyl, propyl, i-propyl, butyl, sec-butyl, n-butyl, pentyl and hexyl groups; the term C$_{3-7}$ cycloalkyl includes cyclopropyl, cyclobutyl, cyclopentyl, cyclohexyl and cycloheptyl rings.

When R$_4$ is phenyl condensed with a heterocyclic ring it is preferably selected from the following formulae:

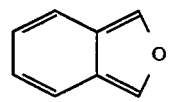

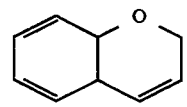

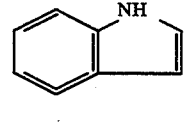

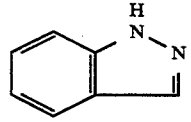

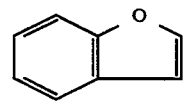

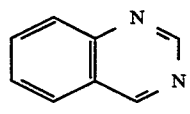

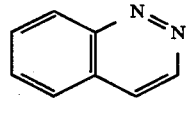

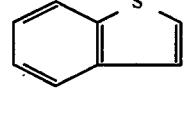

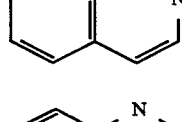

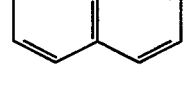

-continued

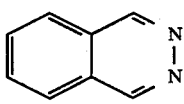

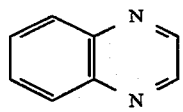

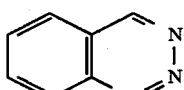

When R₄ is a heterocyclic ring it is preferably chosen from the following formulae:

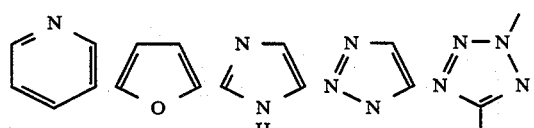

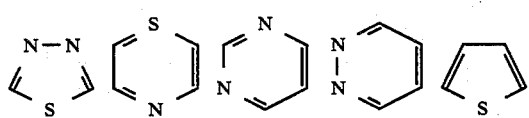

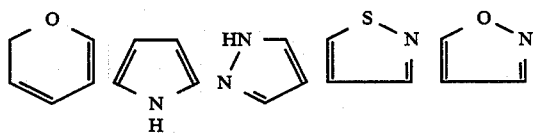

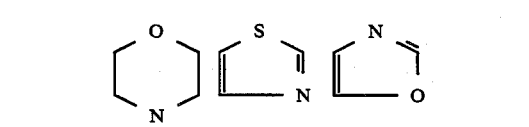

All the heterocyclic ring systems above, optionally substituted, may be totally or partially reduced.

The more preferred compounds of formula I are those wherein $R_1$ is hydrogen or methyl, $R_2$ is hydrogen, bromine or an S-$C_{1-4}$ alkyl group, $R_3$ is methyl, n is 0,1 or 2, and A is selected from OH, $NH_2$, $COOR_3'$, $NHCO_2R_4$, $NHCONHR_4$, $CONHR_4$, $OCONHR_4$, $NHCONHCOR_4$, $NHCSNHCOR_4$

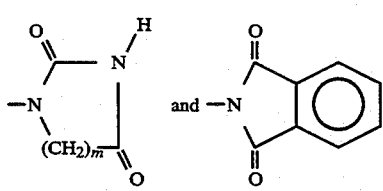

wherein m is 1 or 2, $R_3'$ is $C_{1-4}$ alkyl or hydrogen, and $R_4$ is phenyl, benzyl, t-butyl, pyridyl, 5-bromopyridyl, ethyl, cyclohexyl, adamantidyl, phenylvinyl, 1,5 dimethyl-3-pyrazyl, 2 methyl-4-thiazolyl, pyrazinyl, pyrimidinyl, thiazolyl or 6-chloro-3-pyridazinyl.

Preferably $R_3'$ is a methyl group.

The present invention also provides a process for the production of the compounds of formula (I) and the acid addition salts thereof, which process comprises
(a) reacting a compound of the formula (II)

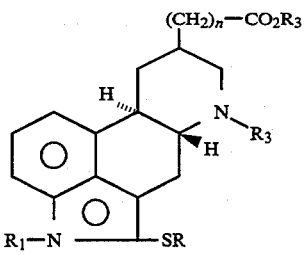

wherein n, $R_1$ and $R_3$ are as above defined and R is $C_{1-4}$ alkyl or phenyl, with a t-butylating agent in the presence of an acid, separating the resultant 13-isomer from the 14-isomer, and removing the 2-SR group by means of a reducing agent;
(i) either hydrolysing the resulting 8-carboxylate and condensing the 8-carboxylic acid produced, optionally after activation, with an amine or formula $R_4$—$NH_2$ wherein $R_4$ is as defined above;
(ii) or reducing the resulting 8-carboxylate and reacting the resulting 8-hydroxymethyl derivative with a compound of the formula $R_4$—N=C=O or with p-nitrophenyl-chlorocarbonate and then with a compound of the formula $R_4$—$NH_2$, wherein $R_4$ is as above defined;
(iii) or reducing the resulting 8-carboxylate and reacting the resulting 8-hydroxymethyl derivative with triphenylphosphine, diethyl-azodicarboxylate and phtalimide, and hydrolysing the compound produced;
(b) reacting the compound obtained in step a(iii), of the formula (III):

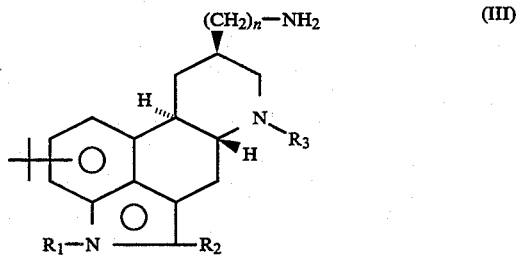

wherein n, $R_1$, $R_2$ and $R_3$ are as defined above, with
(i) a compound of the formula (IV) $R_4$—COOH, wherein $R_4$ is as defined above, or a reactive functional derivative thereof; or
(ii) a compound of the formula (V) $R_4$—N=C=X, or (ii') p-nitrophenyl chlorocarbonate, and reacting the compound produced in either case with a compound of the formula $R_4$—$NH_2$, wherein $R_4$ and X are as above defined; or
(iii) a compound of the formula (VI) Hal-$(CH_2)_m$—COO—$C_{1-2}$ alkyl, wherein m is as above defined and Hal is halogen, and cyclizing the resultant compound with a compound of the formula $R_5$—N=C=X wherein $R_5$ and X are as above defined; or (iv) a compound of formula (VII) R$_4$OCOY wherein R$_4$ is as defined above and Y is chlorine or a p-nitrophenyl group; or (v) a compound of the formula (VIII) R$_4$—CON=C=X. wherein X and R$_4$ are as above defined;

(c) if desired, converting the compound of formula (I) thus produced into another compound of formula (I) and/or, if desired, converting a free compound of formula (I) into an acid addition salt thereof; and (d) recovering the resulting compound of formula (I) as such or as an acid addition salt thereof.

The t-butylating agent used in step (a) may be, for example, isobutene or t-butyl acetate. A suitable acid for this step is trifluoroacetic acid. A suitable reducing agent for step (a) is Raney nickel.

When the 8-carboxylic acid produced in step (a)(i) is activated, it is suitably activated by reaction with a compound such as mixed anhydride, acylazide or N,N'-substituted isourea.

A compound of the formula (I) wherein R$_2$ is hydrogen may be chlorinated or brominated to produce the corresponding compound of formula (I) wherein R$_2$ is chlorine or bromine.

A compound of formula (I) wherein R$_1$ is hydrogen may be N-alkylated to produce a corresponding compound of formula (I) wherein R$_1$ is C$_{1-4}$ alkyl.

A compound of the formula (I) wherein substituent X in the A substituent represents sulphur may be converted to the corresponding compound of formula (I) wherein X is oxygen by treatment with a silver salt.

Process step (b) may be carried out in accordance with a standard procedure. Suitable reactive functional derivatives of compounds of the formula (IV) include the corresponding acyl halides, imidazolides, acylazides. Reaction with acylhalides is suitably effected in the presence of an organic base such as pyridine or triethylamine. Reaction with imidazolides (obtained by reaction of the compounds of formula (IV) with N,N-carbonyldiimidazole) is suitably carried out in an inert solvent such as tetrahydrofuran. Reaction with acylazides (obtained by reaction of a compound of formula (IV) with diphenylphosphoroylazide, DPPA) is suitable carried out in an inert solvent such as tetrahydrofuran at 0° C. in the presence of an organic base such as triethylamine.

Reaction with compounds of the formula (V) or (VIII) (obtainable for example starting from the compound of formula (IV) by known reactions) is suitably carried out in an inert solvent such as tetrahydrofurane or dioxane at a temperature ranging from 65° to 100° C.

The reaction with p-nitrophenylchlorocarbonate may be carried out in an inert solvent such as tetrahydrofurane or methylenchloride, at a temperature of from 0° C. to 30° C., in the presence of a base such as triethylamine or potassium carbonate.

The reaction with a compound of the formula R$_4$—NH$_2$ under (ii') or the reaction with compounds of formula (VI) is suitably carried out in an inert solvent such as dimethylformamide or tetrahydrofurane, at a temperature of from 30° C. to 100° C.

The cyclization under (iii) is preferably carried out by heating in a solvent like dioxane or toluene, or by melting under vacuum.

Reaction with a compound of the formula (VII) is carried out in an inert solvent such as pyridine or tetrahydrofuran at room temperature in the presence of an organic base such as triethylamine.

The chlorination or bromination of a compound of formula (I) wherein R$_2$ is hydrogen may be carried out in accordance with the known methodologies, using standard chlorinating agents or brominating agents such as N—Cl or N—Br succinimide or sulphurylchloride. The reaction is conveniently carried out in an inert solvent such as chloroform, methylene chloride or tetrahydrofuran.

The N-alkylation of a compound of formula (I) wherein R$_1$ is hydrogen may be carried out in accordance with the known methodologies for the N-alkylation of indoles, for instance by employing a compound of formula (IX) R$_1$—Z wherein R$_1$ is C$_{1-4}$ alkyl and Z is a leaving group such as chlorine, bromine, iodine. The reaction is conveniently carried out in an inert solvent such as dimethylsulphoxide and in presence of a strong base such as potassium or sodium hydroxide.

The conversion of substitutent X from sulphur to oxygen may be carried out in a suitable solvent such as ethanol or methansulphonic acid solution in water, the silver salt being silver nitrate or sulphate.

The starting compounds of the formulae (II), (IV), (V), (VI), (VII), (VIII), (IX) and the amine or the formula R$_4$NH$_2$ are known compounds or may be prepared by means of well known procedures starting from known compounds.

The compounds of the present invention display remarkable pharmaceutical properties. Binding assays show that the compounds of the general formula (I) possess high and selective affinity towards 5-HT$_{1A}$ receptor sites having an agonist or antagonist activity at central level. The compounds of the present invention can find use on the management of anxiety, depression, schizophrenia and pain (Pharmacology and Toxicology 1989, 64, p.3–5, Drug of the future 1988, 13 (5), p 429–437, J. Neural Transm. 1988, 74, p.195–198) for the treatment of stress (Neuropharmac, 1989, 25,(5), p.471–476), alleviation of the drug withdrawal (abstinence syndrome) due to the suppression of benzodiazepines, cocaine, alcohol and nicotine, or modification of the food intake and sexual behaviour (J.Receptor Research, 1988,8, p. 59–81), and to alleviate the neuronal damage following cerebral ischemia, acting as neuroprotectant agents (Stroke 1990, 21 (IV) p. 161; J.Cereb. Blood Flow Metabol. 1991, 11(II), p. 426; Pharmacology of cerebral ischemia, 1990, Suttgart 1990, p.493–497)

The following experiments illustrates the binding profile of the compounds of general formula I.

Experiment 1: affinity for serotonin 1A (5-HT$_{1A}$) receptor [$^3$H-8-Hydroxy-2-dipropylaminotetralin ($^3$H-8-OH-DPAT)binding test]

Preparation of crude synaptosome fraction and binding assay were conducted in accordance with the method reported in Journal of Neurochemistry, vol 44, page 1685, 1985 by Hall et al. Freezed hippocampus dissected out from rats were homogenized in 40 volumes of ice cold 50 mM Tris-HCl buffer (pH. 7.4) and the suspension was centrifuged at 500×g for 10 minutes at 0° C. The supernatant was centrifuged at 40,000×g for 20 minutes at 0° C. and the resulting pellet was homogenized in 40 volumes of the above buffer and incubated at 37° C. for 10 minutes. After completion of reaction, the suspension was centrifuged at 40,000×g for 20 minutes at 0° C. The resulting pellet was washed twice by resuspension in 40 volumes of the above buffer and centrifugation, and finally suspended in 60 volumes of ice-cold 50 mM Tris-HCl buffer (pH 7.4) containing 1 mM manganese chloride for use in the next assay.

To the aliquots (900 µl) of synaptosome membranes solution were added 50 µl of tritiated 8-OH-DPAT solution at the terminal concentration of 0.2 nM and 50 µl of test compound solution or 50 µl of its medium, and incubated at 37° C. for 10 minutes. Then to the mixture was added 5 ml of ice-cold 50 mM Tris-CHl buffer (pH 7.4) rapidly vacuum-filtered through Whatman® GF/B filters and was washed twice with 5 ml of the same buffer. The radioactivity of the residue remaining on the filters was measured by liquid scintillation counter. Nonspecific binding was determined under the presence of $10^{-5}M$ serotonin (5-HT). 50% Inhibition concentration ($IC_{50}$) of the test compound was graphically determined. The results are summarized in the table I.

Experiment 2: affinity for serotonin 2(5-HT$_2$)receptor ($^3$H-Ketanserin binding test).

Preparation of crude synaptosome fraction and binding assay were conducted according to the method reported in Molecular Pharmacology, vol.21, page 301, 1981 by Leysen et al.

Freezed cerebral cortex dissected out from rats were homogenized in 30 volumes of ice-cold 0.32M sucrose solution and the suspension was centrifuged at 1000×g for 10 minutes at 0° C. The supernatant was centrifuged at 40,000×g for 10 minutes at 0° C. and the resulting pellets was homogenized in 30 volumes of ice-cold 50 mM Tris-HCl buffer (pH.7.7) and incubated at 37° C. for 10 minutes. The suspension was centrifuged at 40,000×g for 20 minutes at 0° C. again. The resulting pellet was homogenized in 100 volumes of the above buffer and provided as synaptosome membranes solution for the next assay.

To the aliquots (900µ) of synaptosome membranes solution were added 50 µl solution of $^3$H-Ketanserin solution at the terminal concentration of 0.2 mM and 50 µl of test compound or its medium, and incubated at 37° C. for 20 minutes. After completion of the reaction, the mixture was rapidly vacuum-filtered through Whatman® GF/B filters. The filters were washed three times with 5 ml of the above buffer, and then the radioactivity of the residue remaining on the filters was measured by liquid scintillation counter. Non specific binding was determined under the presence of 10 µM of mianserin. 50% Inhibition concentration ($IC_{50}$) of the test compound was graphically determined. The results are summarized in the Table I.

Experiment 3: affinity for dopamine 2 (D$_2$)receptor ($^3$H-Spiperone binding test.)

Preparation of crude synaptosome fraction and binding assays were conducted in accordance with the method reported in European Journal of Pharmacology, vol 46, page 377,1977 by I. Creese et al. Freezed corpus striatum dissected out from rats were homogenized in 100 volumes of ice cold 50 mM Tris-HCl buffer (pH.7.7) and the suspension was centrifuged at 500×g for 10 minutes at 0° C. The supernatant was centrifuged at 50,000×g for 15 minutes at 0° C. and the resulting pellet was homogenized in 100 volumes of the above buffer and then the suspension was centrifuged at 50,000×g for 15 minutes at 0° C. again. The resulting pellet was homogenized in 150 volumes of 50 mM Tris-HCl buffer (PH 7.1) containing 120 mM potassium chloride, 2 mM calcium chloride, 1 mM magnesium chloride, 0,1% ascorbic acid and 10 µM pargyline. The suspension was incubated at 37° C. for 10 minutes and then provided as synaptosome membranes solution for the next assays.

To the aliquots (900µ) of synaptosome membranes solution were added 50 µl of $^3$H-Spiperone solution at the terminal concentration of 0.2 nM and 50 µl of test compound solution or 50 µl of its medium, and incubated at 37° C. for 20 minutes. After completion of the reaction, the mixture was rapidly vacuum-filtered through Whatman® GF/B filters. The filters were washed three times with 5 ml of the above buffer, and then the radioactivity of the residue remaining on the filters was measured by liquid scintillation counter. Nonspecific binding was determined under presence of 100 µM of (L)-Sulpiride 50% Inhibition concentration ($IC_{50}$) of the test compound was graphically determined. The results are summarized in the Table I.

Behavioural Pharmacology

The potential anxiolitic activity of the compounds of the formula I was assessed in a screening model of anxiety, the stress-induced hyperthermia (Lecci A, Borsini F, Volterra G, and Meli A. Pharmacological Validation of a novel animal model of anticipatory anxiety in mice. Psychopharmacology, 1990,101, 255–261). This procedure is based upon the antagonism of an increase in rectal temperature observed in group-caged mice as they are being removed from their cohorts.

From the obtained data shown in the Table II, it is evident that the compounds of this invention are able to antagonize the stress-induced hyperthermia showing potential anxiolitic properties.

TABLE I

| EXAMPLE No OF TEST COMPOUND | RECEPTOR BINDING I-C$_{50}$ µM | | |
|---|---|---|---|
| | D$_2$ | 5-HT$_{1A}$ | 5-HT$_2$ |
| 1 | 5.2 | 0.03 | 6.7 |
| 2 | 2.77 | 0.01 | 1.87 |
| 3 | 4.45 | 0.01 | 1.1 |
| 4 | 3.33 | 0.01 | 0.7 |
| 5 | 1.1 | 0.01 | 3.27 |
| 6 | 1.25 | 0.008 | 0.7 |
| 7 | 5.1 | 0.01 | 1.2 |
| 8 | 2.9 | 0.08 | 2.1 |
| 9 | 2.1 | 0.01 | 1.1 |
| 10 | 3.6 | 0.06 | 2.48 |
| 11 | 3.1 | 0.05 | 3,48 |
| 12 | 2.1 | 0.01 | 6.15 |
| 13 | 1.7 | 0.005 | 1.1 |

TABLE II

| Compound Example | Stress induced hyperthermia ED$_{50}$ (mg/Kg), Mouse, ip |
|---|---|
| 5 | 0.03 |
| 7 | 0.06 |
| 9 | 0.03 |
| 16 | 0.06 |
| 11 | 0.06 |
| 6 | 0.06 |
| 17 | 0.06 |

The toxicity of the compounds of the present invention is quite negligible, and they are therefore safely employable as useful drugs.

A patient is treated according to the present invention by a method comprising administering to the patient an effective amount of a compound of formula I or a pharmaceutically acceptable salt thereof. In this way a compound of formula I or its pharmaceutically acceptable salt can be used to control conditions attributable to serotoninergic disfunctions such as the impairment of thermoregulation or memory function, sleep disorders, drug addiction, hypertension, hyperemesis, depression, anxiety or psychosis, or the control of satiety or drug withdrawal, cerebral ischemia.

The invention further provides a pharmaceutical composition comprising an ergoline derivative having the general formula I or a pharmaceutically acceptable salt thereof in admixture with pharmaceutically acceptable diluent or carrier.

Compounds of formula I and their salts described herein may be administered by parenteral or oral route, preferably by oral route. Depending on administration route, the compositions may be in the form of solid, semi-solid or liquid dosage form, such as, for example, tablets, pills, capsules, powders, liquids, suspension, or the like. The compositions will include a conventional pharmaceutical carrier, adjuvants, etc.

The dosage of the present drugs varies in accordance with the sex, age, condition or medical records of the patients, as well as according to the route or the purpose of the administration. In general, the drugs may be administered as single doses or as divided doses so as to provide, say, about 0.1–10 mg/kg body weight per day of effective ingredients, preferably about 0.1–5 mg/kg body weight.

The pharmaceutical compositions containing the compounds of the invention are prepared according to conventional methods with the usual ingredients.

Thus, for oral administration, the pharmaceutical compositions containing the compounds of the invention are preferably tablets, pills or capsules which contain the active substance together with diluents, such as, for instance, lactose, dextrose, mannitol, sorbitol, sucrose, cellulose, lubricants, for example, silica, talc, stearic acid, magnesium or calcium stearate and or polyethylenglycols; or they may also contain binders, such as, for example, starches, gelatine, methylcellulose, gum arabic, tragacanth, polyvinylpyrrolidone; disintegrating agents, such as, for instance, starches, alginic acid, alginates; effervescing mixture; dyestuff; sweeteners; wetting agents, such as, for instance, lecithin, polysorbates, laurylsulphates, and in general non-toxic and pharmacologically inactive substances used in pharmaceutical formulations. Said pharmaceutical preparations may be manufactured in known manner, for instance, by mean of mixing, granulating, tabletting, sugar-coating, or film-coating processes.

Also the said pharmaceutical formulations containing the compounds of the invention may be prepared by known methods and they can be, for example, syrup or drops for the oral administration, sterile solution for injection, or suppositories.

The following examples illustrate the invention.

EXAMPLE 1

2-Thiomethyl-6-methyl-8β-methoxycarbonyl (13,14)-t-butyl-ergoline. (I, $R_1$=H, $R_2$=SCH$_3$, $R_3$=CH$_3$, A=CO$_2$CH$_3$, n=0)

To a solution of 23 g of 2-thiomethyl-6-methyl-8β-methoxycarbonyl-ergoline in 230 ml of trifluoroacetic acid were added dropwise 24.5 ml of t-butylacetate. The resulting solution was heated at 40° C. for 5 hours. The solvent was evaporated off and the dark residue was taken up in ethylacetate and partitioned with ammonium hydroxyde 0.1N. The organic phase was washed with brine and dried (Na$_2$SO$_4$). The solvent was removed and the foaming residue was dissolved in the minimum amount of methanol. By cooling 13.7 g of the 13 derivative crystalized m.p. 259°–261.° C. By chromatographying the mother liquor, 4.2 g of the corresponding 14-derivative were obtained, m.p. 280°–283° C.

EXAMPLE 2

6-Methyl-8β-methoxycarbonyl-13-t-butyl-ergoline(I, $R_1$=$R_2$=H, $R_3$=CH$_3$, A=CO$_2$CH$_3$, n=0)

To a refluxing solution of 5.75 g of 2-thiomethyl-6-methyl-13-t-butyl-ergoline in 300 ml of methanol were added portionwise 10 g of Ni-Raney under nitrogen.

After 10 minutes reflux, the boiling mixture was filtered and the Ni-Raney was thoroughly washed with methanol.

The solvent was removed and the residue was crystallized from ethylacetate affording 4.3 g of the title compound, m.p. 175°–177° C.

EXAMPLE 3

6-Methyl-8β-hydroxymethyl-13-t-butyl-ergoline (I, $R_1$=$R_2$=H, $R_3$=CH$_3$, A=OH, n=1)

To a solution of 4.5 g of sodium borohydride in 50 ml of methanol were added dropwise a solution of 4.5 g of 6-methyl-8β-methoxy-carbonyl-13-t-butyl-ergoline in 30 ml of methanol. The resulting stirred suspension was heated at 50° C. for 1 hour. The resulting clouding solution was diluted with 200 ml of water, then extracted with chloroform. The organic phase was washed with brine and dried. Evaporation of the solvent and crystallization from ethanol afforded 3.3 g of the title compound, m.p. 240°–243° C.

EXAMPLE 4

6-Methyl-8β-aminomethyl-13-t-butyl-ergoline (I, $R_1$=$R_2$=H, $R_3$=CH$_3$, A=NH$_2$, n=1)

To a stirred suspension of 3 g of 6-methyl-8β-hydroxymethyl-13-butylergoline and 3 g of triphenylphosphine and 2 g of phtalimide in 30 ml of tetrahydrofuran were added dropwise a solution of 2.35 g of diethylazodicarboxylate in 20 ml of tetrahydrofuran.

The stirring was continued for 2 hours; then the resulting orange solution was diluted with 200 ml of methanesulphonic acid 0.1N and extracted with ethylacetate. The acqueous phase was basified with ammonium hydroxyde then extracted with ethylacetate. After washing with brine and drying the solution was concentrated in vacuo affording 4 g of 6-methyl-8β-phtalimido methyl-13-t-butylergoline, m.p. 132°–137° C. To a solution containing this phtalimido derivative in ml 100 of ethanol were added 10 ml of hydrazine hydrate 98%. After stirring for 3 hours, the suspension was filtered off and the filtrate, after evaporation of the solvent was dissolved in ethylacetate and the solution thoroughly washed with sodium hydroxyde 0.1N. The organic phase was washed with brine and dried. Concentration of the solution was afforded 2.4 g of the title compound, m.p. 231°–233° C.

EXAMPLE 5

6-Methyl-8β-benzoylaminomethyl-13-t-butyl-ergoline (I,$R_1$=$R_2$=H, $R_3$=CH$_3$, A=NHCOPh, n=1)

To a solution of 2 g of 6-methyl-8β-aminomethyl-13-t-butyl-ergoline in ml 50 of pyridine was added 0.95 g of benzoylchloride. After stirring at room temperature for 3 hours, the resulting solution was diluted with ethylacetate and washed with a solution of sodium hydroxide 0.1N, then with brine. After drying, the solvent was removed and the residue dissolved in methanol charcolized and then crystallized twice from acetone, affording 2.4 g of the title compound, m.p. 190°–193° C.

EXAMPLE 6

6-Methyl-8β.phenylacetylaminomethyl-13-t-butyl-ergoline (I, $R_1=R_2=H$, $R_3=CH_3$, $A=NHCOCH_2Ph$, n=1).

Operating as in Example 5, but employing phenylacetylchloride instead of benzoyl chloride, the title compound was obtained in 74% yield, m.p. 165°–167° C.

EXAMPLE 7

6-Methyl-8β-pivaloylaminomethyl-13-t-butyl-ergoline (I, $R_1=R_2=H$, $R_3=CH_3$, $A=NHCO+$, n=1)

Operating as in Example 5, but employing pivaloylchloride instead of benzoylchloride, the title compound was obtained in 60% yield, m.p. 235°–238° C.

EXAMPLE 8

6-Methyl-8β-isonicotinoylaminomethyl-13-t-butyl-ergoline (I,$R_1=R_2=H$, $R_3=CH_3$, $A=NHCOC_5H_4N$, n=1)

Operating as in Example 5, but employing isonicotinoyl chloride hydrochloride instead of benzoyl chloride, the title compound was obtained in 45% yield, m.p. 241°–243° C.

EXAMPLE 9

6-methyl-8β-(5-bromo-nicotinoyl)aminomethyl-13-t-butyl-ergoline (I,$R_1=R_2=H$, $R_3=CH_3$, $A=NHCOC_5H_3NBr$, n=1).

Operating as in Example 5, but employing 5-bromonicotinoyl chloride hydrochloride instead of benzoylchloride, the title compound was obtained in 75% yield, m.p. 285°–287° C.

EXAMPLE 10

6-Methyl-8β-benzyloxycarbonylaminomethyl-13-t-butyl-ergoline (I,$R_1=R_2=H$, $R_3=CH_3$, $A=NHCOOPh$, n=1).

Operating as in Example 5, but employing benzyloxycarbonyl chloride instead of benzoylchloride, the title compound was obtained in 55% yield, m.p. 139°–142° C.

EXAMPLE 11

6-Methyl-8β-ethoxycarbonylaminomethyl-13-t-butyl-ergoline (I,$R_1=R_2=H$, $R_3=CH_3$, $A=NHCO_2C_2H_5$, n=1)

Operating as in Example 5, but employing ethoxycarbonylchloride instead of benzoyl chloride, the title compound was obtained in 80% yield, m.p. 235°–237° C.

EXAMPLE 12

6-Methyl-8β-phenylaminocarbonylaminomethyl-13-t-butyl-ergoline (I,$R_1=R_2=H$, $R_3=CH_3$, $A=NHCONHPh$, n=1)

To a solution of 3.2 g of 6-methyl-8β-aminomethyl-13-t-butyl-ergoline in ml 50 of dioxane was added 1.5 g of phenyl isocyanate. The resulting solution was refluxed for 1 hour. The solvent was removed and the residue was chromatographed on a pad of silica gel eluting with chloroform. After evaporation of the solvent and crystallization from ethanol the title compound was obtained in 70% yield, m.p. 238°–240° C.

EXAMPLE 13

6-Methyl-8β-cyclohexylcarbonylaminomethyl-13-t-butyl-ergoline (I=$R_1=R_2=H$, $R_3=CH_3$, $A=NHCOC_6H_{11}$, n=1)

To a solution of 1.92 g of cyclohexancarboxylic acid in ml. 30 of tetrahydrofuran were added 1.7 g of carbonyldiimidazole. The resulting solution was heated at 50° C. for 10′. To the resulting clear solution 3.1 g of 6-methyl-8β-aminomethyl-13-t-butyl-ergoline was added and the heating was continued for 3 hours. The solvent was evaporated off, and the residue was taken up in ethylacetate and washed with a saturated solution of sodium hydrogenocarbonate. After washing with brine and drying, the resulting solution was concentrated affording 3.8 g of the title compound, m.p. 151°–154° C.

EXAMPLE 14

6-Methyl-8β-(1-adamantyl)carbonylaminomethyl-13-t-butyl-ergoline (I;$R_1=R_2=H$, $R_3=CH_3$, $A=NHCOAd$, n=1)

Operating as in Example 13 but employing adamantane-1-carboxylic acid instead of cyclohexan-carboxylic acid, the title compound was obtained in 60% yield, m.p. 240°–243° C.

EXAMPLE 15

6-Methyl-8β-(3-phenyl)acryloylaminomethyl-13-t-butyl-ergoline (I;$R_1=R_2=H$, $R_3=CH_3$, $A=NHCOC_2H_2Ph$, n=1)

Operating as in Example 13, but employing 3-(phenyl)acrylic acid instead of cyclohexan carboxylic acid, the title compound was obtained in 35% yield, m.p. 190°–191° C.

EXAMPLE 16

6-Methyl-8β-(1,5-dimethyl-3-pyrazoyl)aminomethyl-13-t-butyl-ergoline (I;$R_1=R_2=H$, $R_3=CH_3$, $A=NHCOC_3HN_2(CH_3)_2$, n=1)

To a solution of 2.2 g of 1.5-dimethylpyrazol-3-carboxylic acid and 1.5 ml of triethylamine in 20 ml of dimethylformamide at 0° C. were added dropwise 1.1 g ethyl chlorocarbonate.

After stirring for 5 minutes, a solution of 3.1 g of 6-methyl-8β-aminomethyl-13-t-butyl-ergoline in 20 ml of dimethylformamide was added dropwise and the resulting solution stirred overnight at room temperature.

After removing the solvent, the residue was taken up in methylen chloride and the solution washed with a solution of sodium hydroxide 0.1N. After washing with brine and drying, the solvent was removed and the residue crystallized twice from acetone leading to 2.7 g of the title compound, m.p. 262°–265° C.

EXAMPLE 17

6-Methyl-8β-(2-methyl-4-thiazoyl)aminomethyl-13-t-butyl-ergoline (I;$R_1=R_2=H$, $R_3=CH_3$, $A=NHCOC_3H_2NS(CH_3)$, n=1)

Operating as in Example 16, but employing 2-methyl-4-thiazolcarboxylic acid instead of 1,5-dimethylpyrazol-3-carboxylic acid, the title compound was obtained in 45% yield, m.p. 265°–268° C.

EXAMPLE 18

6-Methyl-8β-benzoylaminoethyl-13-t-butyl-ergoline (I;$R_1=R_2=H$, $R_3=CH_3$, $A=NHCOPh$, n=2).

Operating as in Examples 1 to 5, but starting from 2-thiomethyl-6-methyl-8β-methoxycarbonylmethyl-ergoline instead of 2-thiomethyl-6-methyl-8β-methoxycarbonyl-ergoline, the title compound was obtained in 55% yield, m.p. 187°–189° C.

EXAMPLE 19

2-Bromo-6-methyl-8β-benzoylaminomethyl-13-t-ergoline (I;$R_1$=H, $R_2$=Br, $R_3$=$CH_3$, A=NHCOPh, n=1).

To a solution of 2 g of 6-methyl-8β-benzoylaminomethyl-13-t-butyl-ergoline in 75 ml of dioxane were added portionwise 0.9 g of N-bromo-succinimide. After stirring at 40° C. for 2 hours, the solvent was removed and the residue was chromatographed on silica gel eluting with ethylacetate.

After crystallization from isopropanol 1.3 g of the title compound were obtained, m.p. 151°–155° C.

EXAMPLE 20

6-Methyl-8β-aminomethyl-14-t-butyl-ergoline (I;$R_1$=$R_2$=H, $R_3$=$CH_3$, A=$NH_2$, n=1, 14 isomer).

Operating as in Examples 2 to 4 but starting from 2-thiomethyl-6-methyl-8β-methoxycarbonyl-14-t-butyl-ergoline, the title compound was obtained, m.p. 215°–217° C.

EXAMPLE 21

6-Methyl-8β-benzoylaminomethyl-14-t-butyl-ergoline (I;$R_1$=$R_2$=H, $R_3$=$CH_3$, A=NHCOPh, n=1, 14 isomer).

Operating as in Example 5, but employing 6-methyl-8β-aminomethyl-14-t-butyl-ergoline, the title compound was obtained in 80% yield, m.p. 173°–175° C.

EXAMPLE 22

6-Methyl-8β-carboxy-13-t-butyl-ergoline (I;$R_1$=$R_2$=H, $R_3$=$CH_3$, A=$CO_2H$, n=0).

To a stirred solution of 6.2 g of 6-methyl-8β-methoxycarbonyl-13-t-butyl-ergoline in 50 ml of methanol was added dropwise 20 ml of NaOH 1M.

After keeping at room temperature for 2 hours, the solvent was removed and the residue diluted in 100 ml of $H_2O$ and treated with 20 ml of HCl 1M. The resulting precipitate was filtered off, washed with water, then crystallized from boiling methanol affording 5.1 g of the title compound, m.p. 237°–239° C.

EXAMPLE 23

6-Methyl-8β-(2-pyrazinyl)aminocarbonyl-13-t-butyl-ergoline (I;$R_1$=$R_2$=H, $R_3$=$CH_3$, A=$CONHC_4H_3N_2$, n=0).

To a solution of 4 g of 6-methyl-8β-carboxy-13-t-butyl-ergoline and 1.7 g of N-hydroxybenzotriazole in 50 ml of dimethylformamide were added 2.5 g of dicyclohexylcarbodiimide and the resulting solution was stirred at 0° C. for half an hour, then left to rise at room temperature and treated with 1.2 g of 2-amino pyrazine. The resulting cloudy solution was heated at 80° C. for 5 hours, then the solvent was removed. The residue was taken up in ethyl acetate and washed with a saturated solution of sodium hydrogenocarbonate. After washing with brine and drying, the solvent was removed and the crude reaction mixture was chromatographed on silica gel eluting with methylen chloride. Crystallization from acetone afforded 3.7 g of the title compound, m.p. 271°–273° C.

EXAMPLE 24

6-Methyl-8β-(2,6-dimethyl-4-pyrimidinyl)aminocarbonyl-14-t-butyl-ergoline (I, $R_1$=$R_2$=H, $R_3$=$CH_3$, A=-$CONHC_4N_2(CH_3)_2$ n=0, isomer 14).

Operating as in Examples 22 and 23, but employing 6-methyl-8β-methoxycarbonyl-14-t-butyl-ergoline instead of 6-methyl-8β-methoxycarbonyl-13-t-butyl-ergoline and 2,6-dimethyl-4-aminopyrimidine instead of 2-aminopyrazine, the title compound was obtained in 45% yield, m.p. 284°–287° C.

EXAMPLE 25

6-Methyl-8β-(2-thiazolidinyl)aminocarbonyl-13-t-butyl-ergoline (I, $R_1$=$R_2$=H, $R_3$=$CH_3$, A=-$CONHC_3H_2NS$, n=0).

Operating as in Example 23, but employing 2-aminothiazole instead of 2-aminopyrazine, the title compound was obtained in 70% yield, m.p. 230°–234° C.

EXAMPLE 26

6-Methyl-8β-(6-chloro-3-pyridazinyl)aminocarbonyl-13-t-butyl-ergoline (I, $R_1$=$R_2$=H, $R_3$=$CH_3$, A=-$CONHC_4H_2N_2Cl$, n=0).

Operating as in Example 23, but employing 6-chloro-3-aminopyridazine, instead of 2-amino-pyrazine, the title compound was obtained in 35% yield, m.p. 257°–259° C.

EXAMPLE 27

6-Methyl-8β-[(1H,3H)-2,4-dioxo-dihydro-1-pyrimidinylmethyl]-13-t-butyl-ergoline (I, $R_1$=$R_2$=H, $R_3$=$CH_3$, A=$C_4H_5N_2O_2$, n=1)

A mixture of 5.1 g of 6-methyl-8β-aminomethyl-13-t-butyl-ergoline and 1.8 ml methyl acrylate in 100 ml of methanol was refluxed for 4 hours. The solvent was evaporated off and the residue was crystallized from ethylacetate to afford 6 g of 6-methyl-8β-N-(2-methoxycarbonylethyl)aminomethyl-13-t-butyl-ergoline, melting at 153°–157° C., (I, $R_1$=$R_2$=H, $R_3$=$CH_3$, A=$NHC_2H_4CO_2CH_3$, n=1).

To a solution of 2.9 g of potassium cyanate in 30 ml of water it was added dropwise a solution of 6 g of 6-methyl-8β-N-(2-methoxycarbonylethyl)aminomethyl-13-t-butyl-ergoline in 120 ml of water and 35 ml of HCl 1N. The reaction mixture was heated at 80° C. for 4 hours and then allowed to stand overnight at room temperature. The solid was separated out, washed with water and crystallized from ethanol to give 4.3 g of the title compound, m.p. 297°–302° C.

EXAMPLE 28

6-Methyl-8β-(2-thiazolidinyl)aminocarbonyl-14-t-butyl-ergoline (I,$R_1$=$R_2$=H, $R_3$=$CH_3$,A=-$CONHC_3H_2NS$,n=0)

Operating as in Example 25, but employing 6-methyl-8β-carboxy-14-t-butyl-ergoline instead of 6-methyl-8β-carboxy-13-t-butyl-ergoline, the title compound was obtained in 60°% yield, m.p. 243°–247° C.

EXAMPLE 29

N-[6-methylergolin-14-t-butyl-8β-yl)methyl]-N'-acetyl-thiourea (I,$R_1$=$R_2$=H, $R_3$=$CH_3$,A=NH—CS—NH-$COCH_3$,n=1)

To a solution of 3.2 g of 6-methyl-8β-aminomethyl-14-t-butyl-ergoline in 30 ml of tetrahydrofuran were added 1.5 g of acetyl isothiocyanate freshly prepared.

After stirring for 3 h, the resulting yellow solution was evaporated to dryness and the residue filtered on a small pad of silica gel eluting with dichloromethane. After crystallization from acetone, the title compound was obtained in 40% yield, m.p. 220°–223° C.

EXAMPLE 30

N-[6-methylergolin-14-t-butyl-8β-yl)methyl]-N'-benzoyl-thiourea (I,$R_1=R_2=H$, $R_3=CH_3$,A=NH-CS—NHCOC$_6$H$_5$,n=1)

Operating as in Example 29, but employing benzoylisothiocyanate instead of acetylisothiocyanate, the title compound was obtained in 75% yield, m.p. 287°–289° C.

EXAMPLE 31

N-[(6-Methylergolin-14-t-butyl-8β-yl)methyl]-N'-benzoyl-urea (I,$R_1=R_2=H$, $R_3=CH_3$,A=NHCONH-COC$_6$H$_5$,n=1)

To a solution of 4.4 g of N-[(6-methylergolin-14-t-butyl-8β-yl)methyl]-N'-benzoyl-thiourea in ml 50 of ethanol was added dropwise a solution of 3.5 g of silver nitrate in 20 ml of water. The resulting black solution was refluxed for 10 minutes then filtered on a pad of celite.

The solvent was removed off and the residue was taken up in ethylacetate. After washing with brine and drying (Mg SO$_4$), the solvent was evaporated and the crude product was crystallized twice from acetone affording 2.8 g of the title compound, m.p. 293°–297° C.

EXAMPLE 32

6-Methyl-8β-benzoylamino-13-butyl-ergoline (I:$R_1=R_2=H$, $R_3=CH_3$,A=NHCOPh,n=0)

Operating as in Example 5, but employing 6-methyl-8β-ammino-13-t-butyl-ergoline instead of 6-methyl-8β-aminomethyl-13-t-butyl-ergoline, the title compound was obtained in 60% yield, m.p. 143°–145° C.

EXAMPLE 33

6-Methyl-8β-(2-furyl)acryloylaminomethyl-13-t-butyl-ergoline (I; $R_1=R_2=H$, $R_3=CH_3$, A=NHCOC$_2$H$_2$C$_4$H$_3$O, n=1)

Operating as in Example 13, but employing 3-(2-furyl)acrylic acid (E) instead of cyclohexancarboxylic acid, the title compound was obtained in 25% yield, m.p. 173°–178° C.

EXAMPLE 34

6-Methyl-8β-(3,4 dimethyoxybenzoyl)aminomethyl-13-t-butyl-ergoline (I;$R_1=R_2=H$,$R_3=CH_3$, A=MH-COC$_8$H$_9$O$_2$, n=1)

Operating as in Example 5, but employing 3,5-dimethoxy benzoylchloride instead of benzoylchloride, the title compound was obtained in 75% yield, m.p. 153°–157° C.

EXAMPLE 35

6-Methyl-8β(1-phenyl-2-pyrrolyl)aminomethyl-13-t-butyl-ergoline (I; $R_1=R_2=H$,$R_3=CH_3$,A=NH-COC$_4$H$_3$NC$_6$H$_5$, n=1)

Operating as in Example 16, but employing 1-phenyl-pyrrol-2-carboxylic acid instead of 1,5-dimethyl-pyrazol-3-carboxylic acid, the title compound was obtained in 35% yield, m.p. 135°–137° C.

EXAMPLE 36

| Tablet preparation | |
|---|---|
| Compound of example 5 (FCE 23892) | 5 mg |
| lactose | 200 mg |
| corn starch | 50 mg |
| Magnesium stearate | 5 mg |

Method of preparation: FCE 23892 lactose and corn starch were mixed and homogenously moistened with water. After screening of the moist mass and dried in a tray drier, the mixture was passed again through a screen and magnesium stearate was added. The resulting mixture was pressed into tablets weighting 260 mg each.

EXAMPLE 37

| Capsule preparation | |
|---|---|
| Compound of example 9 (FCE 27823) | 5 mg |
| lactose | 200 mg |
| Magnesium stearate | 5 mg |

Method of preparation: FCE 27823 was mixed with the auxiliary products, and the resulting mixture was passed through a screen and mixed homogeneously in a suitable device. The resulting mixture was filled into hard gelatine capsule (210 mg per capsule).

We claim:
1. A compound of the formula (I)

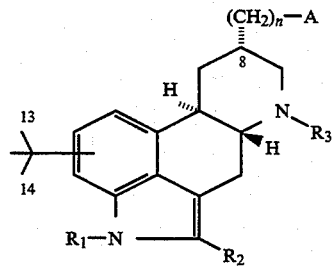

wherein A represents OH, NH$_2$, COOR'$_3$, OCONHR$_4$, CONHR$_4$, NHCOR$_4$, NHCO$_2$R$_4$, NHC(X)NHR$_4$, NHC(X)NHCOR$_4$,

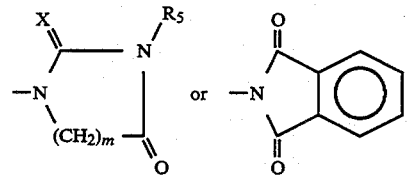

R$_1$ is hydrogen or C$_{1-4}$ linear or branched alkyl; R$_2$ is hydrogen, chlorine, bromine or an S—C$_{1-4}$ alkyl group; R$_3$ and R$_3$' are, independently, C$_{1-5}$ alkyl or hydrogen, n is 0, 1 or 2; m is 1 or 2; R$_4$ is hydrogen, C$_{1-7}$ alkyl, C$_{3-7}$ cycloalkyl, adamantidyl (tricyclo 3.3.1.1.$^{3,7}$) decan-1-yl, C$_{1-5}$-alkylphenyl, C$_2$-alkenyl-phenyl; C$_2$-alkynyl-phenyl, phenyl optionally substituted by one or more groups selected from C$_{1-4}$ alkyl, C$_{1-3}$ alkoxy, methylendioxy, cyano, trifluoromethyl, hydroxy, nitro and acetyl; a heterocyclic group selected from the group consisting of pyridyl, pyrazolyl, thiazolyl, pyrazinyl, pyrmidinyl, pyridazinyl, furyl and pyrrolyl, each of which is optionally substituted by a group selected from $C_{1-4}$ alkyl, phenyl optionally substituted as defined above, $C_{1-3}$ alkoxy and halogen; $R_5$ is hydrogen, $C_{1-4}$ alkyl or a phenyl group and X is NH, O, or S; or a pharmaceutically acceptable salt thereof.

2. A compound according to claim 1 wherein $R_1$ is hydrogen or a methyl group, $R_2$ is hydrogen, bromine or a S—$C_{1-4}$ alkyl group, $R_3$ is methyl, n is 0, 1 or 2, and A is selected from OH, $NH_2$, $COOR_3'$, $NHCO_2R_4$, $NHCONHR_4$, $CONHR_4$, $OCONHR_4$, $NHCONHCOR_4$, $NHCSNHCOR_4$

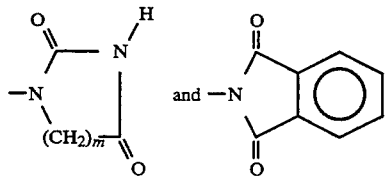

wherein m is 1 or 2, $R_3'$ is $C_{1-4}$ alkyl or hydrogen and $R_4$ is phenyl, benzyl, t-butyl, pyridyl, 5-bromopyridyl, ethyl, cyclohexyl, adamantidyl, phenylvinyl, 1,5 dimethyl-3-pyrazyl, 2 methyl-4-thiazolyl, pyrazinyl, pyrimidinyl, thiazolyl or 6-chloro-3-pyridazinyl.

3. A process for preparing a compound of the formula (I) as defined in claim 1 or 2, which process comprises:
   (a) reacting a compound of the formula (II)

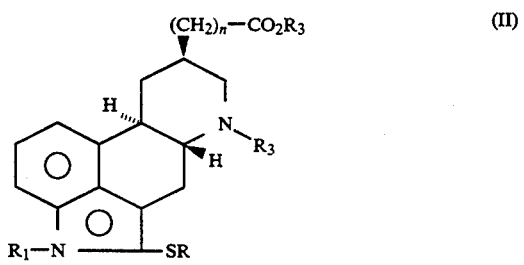

wherein n, $R_1$ and $R_3$ are as defined in claim 1 or 2 and R is $C_{1-4}$ alkyl or phenyl, with a t-butylating agent in the presence of an acid, separating the resultant 13-isomer from the 14-isomer and removing the 2-S—R group by means of a reducing agent;
   (i) either hydrolysing the resulting 8-carboxylate and condensing the 8-carboxylic acid produced, optionally after activation, with an amine of the formula $R_4$—$NH_2$ wherein $R_4$ is as defined in claim 1 or 2;
   (ii) or reducing the resulting 8-carboxylate and reacting the resulting 8-hydroxymethyl derivative with a compound of the formula $R_4$—N=C=O or with p-nitrophenylchlorocarbonate and then with a compound of the formula $R_4$—$NH_2$, wherein $R_4$ is as above defined;
   (iii) or reducing the resulting 8-carboxylate and reacting the resulting 8-hydroxymethyl derivative with triphenylphosphine, diethylazodicarboxylate and phtalimide, and then hydrolysing the compound produced;
   (b) reacting the compound obtained in step a(iii) of the formula (III)

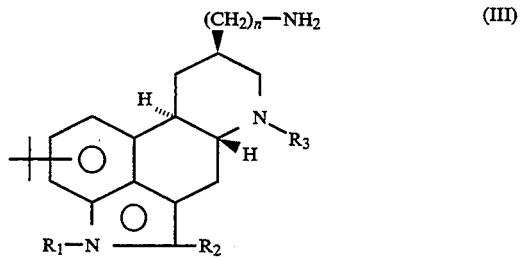

wherein n, $R_1$, and $R_3$ are as defined above and $R_2$ is as defined in claim 1 or 2, with
   (i) a compound of the formula (IV) $R_4$—COOH, wherein $R_4$ is as defined above, or a reactive functional derivative thereof; or
   (ii) a compound of the formula (V) $R_4$—N=C=X, or (ii') p-nitrophenyl chlorocarbonate, and reacting the compound produced in either case with a compound of the formula $R_4$—$NH_2$ wherein $R_4$ and X are as above defined; or
   (iii) a compound of the formula (VI) Hal-$(CH_2)_m$—COO—$C_{1-2}$ alkyl, wherein m is as above defined and Hal is halogen, and cyclizing the resultant compound with a compound of the formula $R_5$—N=C=X wherein $R_5$ and X are as defined in claim 1 or 2; or
   (iv) a compound of formula (VII) $R_4OCOY$ wherein $R_4$ is as defined above and Y is chlorine or a p-nitrophenyl group; or (v) a compound of formula (VIII) $R_4CON$=C=X, wherein X and $R_4$ are as above defined;
   (c) if desired, converting the compound of formula (I) thus produced into another compound of formula (I) and/or, if desired, converting a free compound of formula (I) into an acid addition salt thereof; and
   (d) recovering the obtained compound of formula (I) as such or as an acid addition salt thereof.

4. A process according to claim 3 wherein step (c) comprises chlorinating or brominating a compound of formula (I) wherein $R_2$ is hydrogen to produce a corresponding compound of formula (I) wherein $R_2$ is chlorine or bromine.

5. A process according to claim 3 or 4 wherein step (c) comprises N-alkylating a compound of formula (I) wherein $R_1$ is hydrogen to produce a corresponding compound of formula (I) wherein $R_1$ is a $C_{1-4}$ alkyl group.

6. A process according to any one of claims 3 to 5 wherein step (c) comprises converting a compound of formula (I) wherein X in substituent A is sulphur into a corresponding compound of formula (I) wherein X is oxygen, by treatment with a silver salt.

7. A pharmaceutical composition which comprises a pharmaceutically acceptable diluent or carrier and, as an active principle, a compound of formula (I) as defined in claim 1 or 2, or a pharmaceutically acceptable salt thereof.

8. A method for treating a pathological condition attributable to serotoninergic disfunction, comprising administering to a subject in need thereof an effective amount of the compound of formula (I) as defined in claim 1 or 2.

* * * * *